US00PP26329P3

(12) United States Plant Patent
Westmoreland

(10) Patent No.: US PP26,329 P3
(45) Date of Patent: Jan. 19, 2016

(54) ***HEMEROCALLIS* PLANT NAMED 'WF 73'**

(50) Latin Name: ***Hemerocallis* hybrid**
Varietal Denomination: WF 73

(71) Applicant: Philip Dale Westmoreland, Franklinton, LA (US)

(72) Inventor: Philip Dale Westmoreland, Franklinton, LA (US)

( * ) Notice: Subject to any disclaimer, the term of this patent is extended or adjusted under 35 U.S.C. 154(b) by 100 days.

(21) Appl. No.: 13/999,583

(22) Filed: Mar. 10, 2014

(65) Prior Publication Data

US 2015/0257324 P1 Sep. 10, 2015

(51) Int. Cl.
*A01H 5/02* (2006.01)

(52) U.S. Cl.
USPC ..... Plt./312

(58) Field of Classification Search
USPC ..... Plt./312
See application file for complete search history.

*Primary Examiner* — Susan McCormick Ewoldt
(74) *Attorney, Agent, or Firm* — Cassandra Bright

(57) ABSTRACT

A new and distinct *Hemerocallis* cultivar named 'WF 73' is disclosed, characterized by its excellent landscape performance, resistance to daylily rust, orange-red flower color, with a yellow throat. Plants bloom very early and have evergreen foliage. The new variety is a *Hemerocallis*, normally produced as an outdoor garden plant.

1 Drawing Sheet

Latin name of the genus and species: *Hemerocallis* hybrid. Variety denomination: 'WF 73'.

BACKGROUND OF THE INVENTION

The new *Hemerocallis* cultivar is a product of a planned breeding program conducted by the inventor Philip Dale Westmoreland, in Southern Louisiana. The objective of the breeding program was to produce new *Hemerocallis* varieties with strong performance in the landscape. This includes such characteristics as clear color, repeat bloom over a long period, strong and upright flower scape, high bud count, fade resistance of blooms, foliage appeal, and maintaining plant vigor throughout the season in a general landscape environment where it may not get optimum care.

Since the advent of daylily rust, beginning in approximately 2000, caused by *Puccinia hemerallidis*, the top priority in the breeding program has been to develop seedlings with a high resistance to daylily rust, in addition to the previously cited characteristics. The selection process involves no application of fungicides on any cultivars in our hybridizing program. This practices results in a loss of many cultivars in the program, but is necessary to determine which varieties may be rust resistant.

All daylilies from this program are hybridized, evaluated, and multiplied in plastic nursery containers using pinebark screenings as a growing medium and using overhead sprinklers for irrigation. They are grown in full sun outdoors year round. Each cultivar selected is confidentially evaluated for a period of 5 to 10 years.

The cross resulting in the variety know as 'WF 73' was made during 2006. The seed parent is an unnamed, unpatented proprietary seedling, as is the pollen parent. The new variety was selected in the September of 2009 by the inventor in a group of seedlings resulting from the 2006 crossing, at a commercial nursery in Franklinton, La.

Asexual reproduction of the new cultivar was first performed by root divisions at a the same commercial nursery in Franklinton, La. during 2009, and has shown that the unique features of this cultivar are stable and reproduced true to type over multiple generations.

SUMMARY OF THE INVENTION

The cultivar 'WF 73' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WF 73'. These characteristics in combination distinguish 'WF 73' as a new and distinct *Hemerocallis* cultivar:

1. Excellent landscape performance
2. Orange-Red flower color, with a yellow throat
3. Very early blooming.
4. Repeat blooming
5. 20 inch scape.
6. Dark green foliage
7. Highly resistant to daylily rust.
8. Evergreen foliage.
9. Deep, consistent attractive margin ruffling.
10. Upright foliage The inventor is unable to compare 'WF 73' to the parent varieties, as it is unknown which proprietary varieties are the actual parents.

COMMERCIAL COMPARISON

Plants of the new cultivar 'WF 73' are comparable to the unpatented commercial variety *Hemerocallis* 'Orange Crush'. The two *Hemerocallis* varieties are similar in most horticultural characteristics; however, the new variety 'WF 73' differs in the following;

1. Rust free.
2. More erect bloom scape.

Plants of the new cultivar 'WF 73' can also be compared to the unpatented commercial variety *Hemerocallis* 'Kwanso' These varieties are similar in most horticultural characteristics; however 'WF 73' differs in the following;

1. Much larger flower.
2. Evergreen foliage. The comparator has foliage that goes dormant in winter.
3. Repeated blooms for 90-100 days. The comparator blooms once only.
4. Very strong upright flower scapes. The comparator flower scape will droop.

BRIEF DESCRIPTION OF THE PHOTOGRAPH

The accompanying photograph in FIG. 1 illustrates in full color a typical plant of 'WF 73' grown outdoors, in a 1 gallon pot. Age of the plant photographed is approximately 1 year old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'WF 73' plants grown outdoors in Camarillo, Calif. The growing temperature ranged from approximately 10° C. to 35° C. during the day and from approximately 5° C. to 23° C. during the night. General light conditions are bright, normal sunlight. Measurements and numerical values represent averages of typical plant types.

Botanical classification: *Hemerocallis* hybrid 'WF 73'.

PROPAGATION

Root description: Rhizomes. Thick, typically colored near Orange-White 159C.

Propagation method: Rhizome divisions or tissue culture.

PLANT

Age of plant described: Approximately 12 months.

Container size: 1 gallon.

Growth habit: Evergreen semi-hardy perennial.

Height: Approximately 48 cm to top of highest leaf Approximately 60 cm to top of highest inflorescence.

Plant spread: Approximately 40 cm.

Growth rate: Moderate to rapid.

Branching characteristics: Non-branching, forms basal clumps.

FOLIAGE

Leaf:

- *Growth habit*.—Mainly upright.
- *Average length*.—Approximately 50 cm.
- *Average width*.—Approximately 2.6 cm.
- *Shape of blade*.—Narrow lanceolate.
- *Apex*.—Acute.
- *Base*.—Truncate.
- *Sheathing*.—No.
- *Margin*.—Entire.
- *Texture of top surface*.—Glabrous with minute ridges.
- *Texture of bottom surface*.—Glabrous with minute ridges and a very prominent mid-vein.
- *Quantity of leaves per plant*.—Average 24.
- *Color*.—Young foliage upper side: Near RHS Green N138A. Young foliage under side: Near RHS Green N138A. Mature foliage upper side: Near RHS Green N138A, but darker. Mature foliage under side: Near RHS Green N138A.
- *Venation*.—Type: Linear. Venation color upper side: Near RHS Green 137A. Venation color under side: Near RHS Green 137A.

FLOWER

Natural flowering season: Typically early Spring until Fall.

Inflorescence type and habit: Single flowers occurring in clusters of 3 to 6 on a scape.

Flower longevity on plant: 2 to 4 days from fully opened.

Quantity of open flowers per plant at one time: Approximately 3 to 12.

Inflorescence size (excluding scape):

- *Height*.—Approximately 18 cm.
- *Width*.—Approximately 20 cm.

Individual corolla:

- *Arrangement*.—Rotate.
- *Size*.—Length: Approximately 15 cm. Width: Approximately 11 cm at widest point.
- *Tepals per corolla*.—6.
- *Margin*.—Entire, with deep, even very attractive ruffling.
- *Tepal shape*.—Ovate.
- *Apex*.—Acute, ruffled.
- *Texture*.—Glabrous, all surfaces.

Color:

- *Tepals*.—When opening: Outer surface: Near RHS Greyed-Orange 170A. Inner surface: Near RHS Orange-Red N30A, tube Yellow 13A. Fully opened: Outer surface: Near RHS Orange 25A. Inner surface: Near RHS Orange-Red N30A, and N30B and Orange-Red 30A and 30B. Streaked with Yellow 12A and Yellow 4D. Tube Yellow 13A. Aging Flower color: Outer surface: Near RHS Orange 25A. Inner surface: Near RHS Orange-Red N30A, and N30B and Orange-Red 30A and 30B. Streaked with Yellow 12A and Yellow 4D and White 155A. Tube Yellow 13A.

Bud:

- *Shape*.—Elongated and oblong.
- *Length*.—Approximately 5.5 cm.
- *Diameter*.—Approximately 1 cm.
- *Color*.—Near RHS Orange 25B.

Scape:

- *Length*.—Approximately 51 cm.
- *Width*.—Approximately 0.8 cm.
- *Angle*.—Upright, straight.
- *Strength*.—Very Strong.
- *Color*.—Near RHS Green 138A, but darker.

Peduncles:

- *Quantity per scape*.—Typically 2 to 6.
- *Length*.—Approximately 5 cm to 12 cm.
- *Width*.—Approximately 0.5 cm.
- *Aspect/angle*.—Approximately 45 degrees.

*Texture*.—Glabrous.
*Color*.—Near Green RHS 138A.

REPRODUCTIVE ORGANS

Stamens:
*Number*.—Average 6.
*Filament length*.—Approximately 8.5 cm.
*Filament color*.—Near RHS Orange 25B.
*Anther length*.—0.4 cm.
*Anther color*.—Near RHS Greyed-Orange 170B.
*Anther shape*.—Symmetrical and oblong.
*Pollen*.—Moderate.
Pistil:
*Number*.—1.
*Length*.—Approximately 9.5 cm.
*Style color*.—Near RHS Orange 25B.
*Stigma*.—Shape: Linear. Color: Near RHS Orange N25A.
*Ovary color*.—Near Green RHS 137A.

OTHER CHARACTERISTICS

Seeds and fruits: None observed to date.
Disease/pest resistance: Common to other *Hemerocallis* varieties.
Temperature tolerance: Tolerates temperatures from approximately below 0° C. to 35° C.
What is claimed is:
1. A new and distinct cultivar of *Hemerocallis* plant named 'WF 73' as herein illustrated and described.

* * * * *

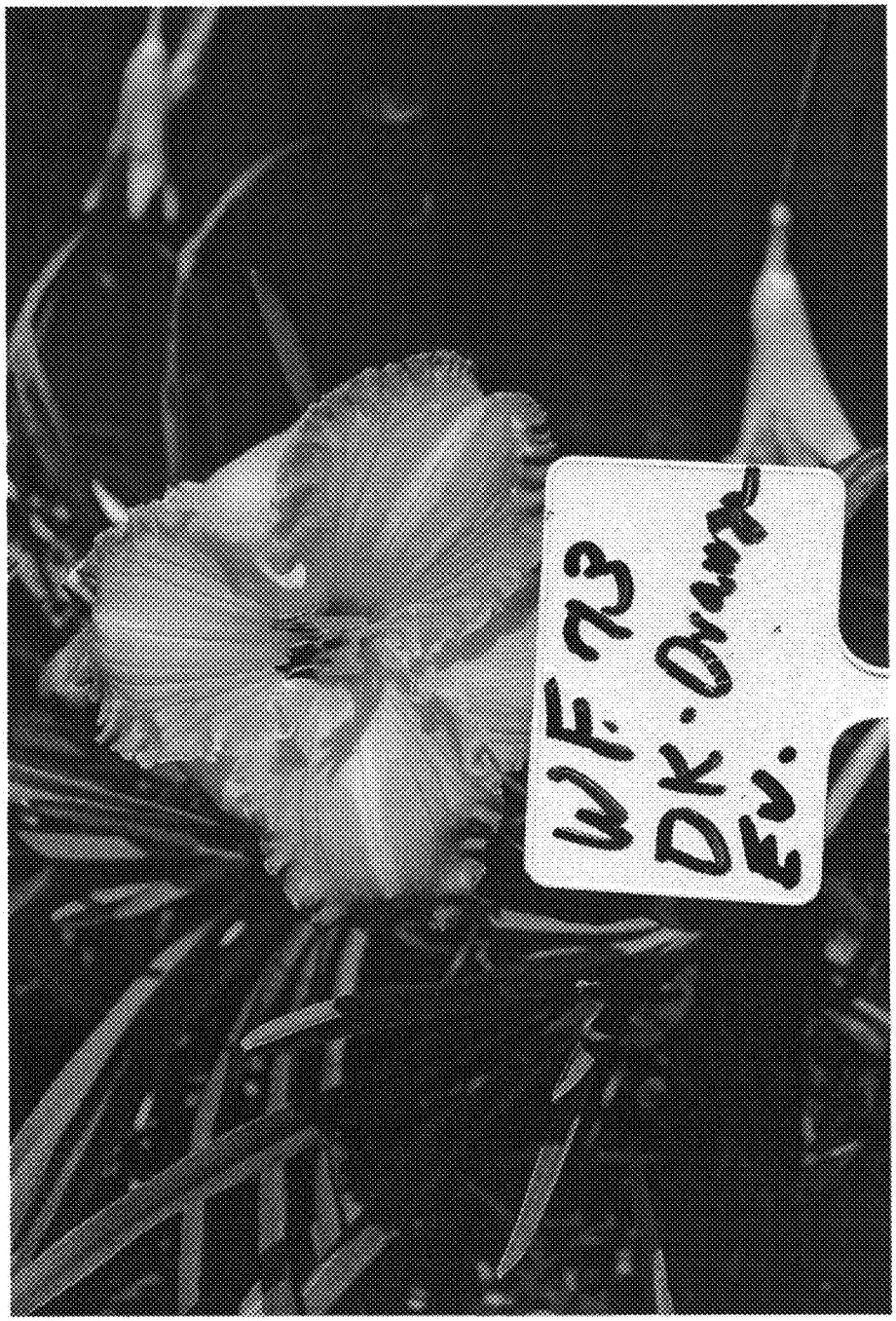
WF 73
DK. Orange
Ev.